United States Patent [19]

Karrer

[11] 4,166,814
[45] Sep. 4, 1979

[54] BIS-POLYALKYLPIPERIDINES

[75] Inventor: Friedrich Karrer, Zofingen, Switzerland

[73] Assignee: Ciba-Geigy Corporation, Ardsley, N.Y.

[21] Appl. No.: 840,706

[22] Filed: Oct. 11, 1977

[30] Foreign Application Priority Data

Oct. 18, 1976 [CH] Switzerland .................. 13164/76

[51] Int. Cl.² .................. C08K 5/34; C07D 211/06; C09B 23/00
[52] U.S. Cl. .................. 260/45.75 N; 260/45.8 N; 542/414; 542/476
[58] Field of Search .................. 260/293.64, 45.8 N, 260/2.5 BB, 270 PD, 45.75 N; 542/414, 476

[56] References Cited

U.S. PATENT DOCUMENTS

| 3,436,368 | 4/1969 | Murray | 260/45.8 N |
| 3,480,635 | 11/1969 | Altwicker | 260/45.8 N |

FOREIGN PATENT DOCUMENTS 259074  5/1970  U.S.S.R. .................. 546/188

OTHER PUBLICATIONS

Textbook of Organic Chemistry, Carl R. Noller, Second Edition, 1961 pp. 40, 41 and 48.

Primary Examiner—Veronica P. Hoke
Attorney, Agent, or Firm—Vincent J. Cavalieri

[57] ABSTRACT

Polyalkylpiperidines of formula I,

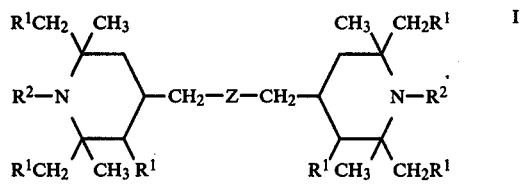

wherein $R^1$ is H or lower alkyl, $R^2$ is H, O or a monovalent organic residue and Z is a divalent aromatic residue, are excellent light stabilizers for plastics. These compounds can be prepared from the according 4-oxopiperidines by Wittig-Horner reaction with diphosphonates of the formula IV,

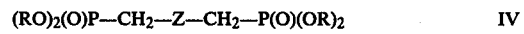

(RO)₂(O)P—CH₂—Z—CH₂—P(O)(OR)₂   IV wherein R denotes lower alkyl, and subsequent hydrogenation of the resulting diolefines. The compounds of formula I are especially suitable for the stabilization of polyolefins, styrene polymers and polyurethanes.

15 Claims, No Drawings

BIS-POLYALKYLPIPERIDINES

The invention relates to new bis-polyalkylpiperidines, their manufacture and their use as light stabilisers for plastics.

It is known that piperidine derivatives alkylated in the 2-position and 6-position are good light stabilisers for plastics. This applies above all to those piperidine derivatives which are substituted in the 4-position, for example by ether, ester, acetal, amide, carbamate, urea or hydantoin groups. Above all, the esters of alkylated 4-piperidinols described in German Offenlegungsschriften Nos. 1,929,928 and 2,258,752 have proved suitable for stabilising polyolefines. However, like most other piperidine light stabilisers substituted in the 4-position, they have the general disadvantage that they are susceptible to hydrolysis. Whilst the stability of additives to hydrolysis has no significance for many fields of application of plastics, there are fields of application where the plastic has a large surface and frequently comes into contact with water, for example in the case of textile fibres or in films which are exposed to weathering. In such cases, hydrolysis of the esters results in the formation of the corresponding 4-hydroxypiperidine, which has a weak light stabilising action and rapidly migrates out of the plastic due to its relatively high volatility.

Polyalkylpiperidines which do not carry a substituent in the 4-position have also already been proposed, for example in German Offenlegungsschrift No. 2,418,540; however, because of their volatility, these have a light stabilising action inferior to that of the piperidines substituted in the 4-position.

The object of the invention was, therefore, to find polyalkylpiperidine derivatives which, whilst having a good light stabilising action, are resistant to hydrolysis and, under the conditions under which the plastics are used, do not migrate out of the plastics to be protected and are not volatile.

It has been found that bis-polyalkylpiperidines in which two piperidine radicals are each bonded in the 4-position, by a C-C bond, to an araliphatic hydrocarbon radical are suitable for this purpose. These compounds, which were hitherto unknown, correspond to the formula I

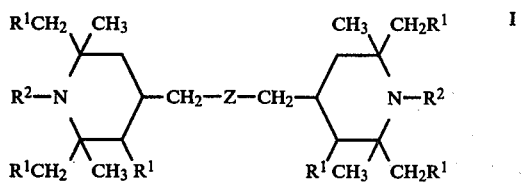

in which $R^1$ denotes hydrogen or alkyl with 1-4 C atoms, $R^2$ denotes hydrogen, an oxyl radical, alkyl with 1-12 C atoms, alkenyl with 3-6 C atoms, alkynyl with 3-6 C atoms, 2,3-epoxypropyl, aralkyl or alkaralkyl with 7-11 C atoms or one of the groups —CO—$R^3$, —CH$_2$COOR$^4$, —COOR$^4$, —CONHR$^5$, —CH$_2$CONHR$^5$ or —CH$_2$CH(R$^6$)OR$^7$, $R^3$ denotes hydrogen, alkyl with 1-6 C atoms, alkenyl with 2-4 C atoms, alkynyl with 2-4 C atoms or aralkyl or alkaralkyl with 7-15 C atoms, $R^4$ denotes alkyl with 1-18 C atoms, alkenyl with 3-6 C atoms, aralkyl with 7-8 C atoms or cyclohexyl, $R^5$ denotes alkyl with 1-18 C atoms, aralkyl or alkaralkyl with 7-15 C atoms, phenyl or alkylphenyl with 6-8 C atoms or cyclohexyl, $R^6$ denotes hydrogen, methyl or phenyl, $R^7$ denotes hydrogen or an alkanoyl, alkenoyl, aroyl or alkaroyl group with up to 18 C atoms and Z denotes a phenylene group or a group of the formula II

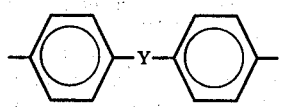

in which Y represents a direct bond or one of the groups —CH$_2$—, —C(CH$_3$)$_2$— or —O—.

The salts of such compounds with inorganic or organic acids and the complexes of the piperidines with nickel compounds are also suitable for this purpose.

When $R^1$ denotes alkyl, this can be, for example, methyl, ethyl, propyl, butyl or isobutyl.

When $R^2$ denotes alkyl with 1-12 C atoms, this can be, for example, methyl, ethyl, propyl, butyl, isobutyl, 2-ethylbutyl, n-hexyl, n-octyl, isooctyl, decyl or dodecyl.

As alkyl with 1-18 C atoms, $R^4$ and $R^5$ can moreover be, for example, tetradecyl, hexadecyl or octadecyl.

When $R^2$ or $R^4$ denotes alkenyl with 3-6 C atoms, this can be, for example, allyl, methallyl, but-2-en-1-yl or hex-2-en-1-yl.

When $R^2$ denotes alkynyl with 3-6 C atoms, this can be, for example, propargyl, but-2-in-1-yl or hex-2-in-1-yl.

When $R^2$ denotes aralkyl or alkaralkyl with 7-11 C atoms, this can be, for example, benzyl, 2-phenylethyl or 4-t-butyl-benzyl.

When $R^2$ is an acyl group —CO—$R^3$, this can be, for example, formyl, acetyl, propionyl, butyryl, acryloyl, methacryloyl, crotonyl, propiolyl, butinoyl, phenylacetyl or phenylpropionyl.

When $R^4$ denotes aralkyl with 7-8 C atoms, this can be, for example, benzyl or phenylethyl.

When $R^5$ denotes aralkyl or alkaralkyl with 7-15 C atoms, this can be, for example, benzyl, phenylethyl, 3-methylbenzyl, 4-butylbenzyl or 4-octylbenzyl. When $R^5$ denotes alkylphenyl, this can be, for example, methyl-phenyl, tert.-butylphenyl or isononyl-phenyl.

When $R^7$ is an alkanoyl, alkenoyl, aroyl or alkaroyl group, this can be, for example, acetyl, propionyl, butyryl, capryl, lauroyl, stearoyl, oleyl, crotonyl, benzoyl, toluyl, butylbenzoyl or naphthoyl.

Compounds of the formula I which are capable of salt formation are those in which the piperidine nitrogen is basic. This is not the case in the compounds in which $R^2$ is —COR$^3$, —COOR$^5$ or —CONHR$^5$. Inorganic acids, such as, for example, hydrochloric acid, sulphuric acid or phosphoric acid, or organic acids, such as, for example, acetic acid, formic acid, salicylic acid, toluenesulphonic acid, diethylphosphoric acid, phenylphosphonic acid or diphenylphosphinic acid, can be used for forming the salts.

Examples of nickel compounds with which the compounds of the formula I can form complexes are nickel chloride, nickel acetate, nickel salicylate, nickel acetylacetonate or nickel bis-(O-ethyl-4-hydroxy-3,5-di-t-butyl-benzylphosphonate).

Compounds of the formula I in which $R^1$ is hydrogen are preferred.

Compounds of the formula I in which $R^2$ denotes hydrogen, alkyl with 1-6 C atoms, alkenyl with 3-5 C atoms, propargyl, benzyl, acetyl, propionyl, butyroyl, acryloyl, methacryloyl or crotonyl, but especially hydrogen, methyl, allyl or benzyl, are also preferred.

Compounds of the formula I in which Z denotes phenylene or para-diphenylene are also preferred.

The following list gives examples of individual compounds of the formula I, without this being intended to restrict the invention to these compounds.

1,4-Bis-(2,2,6,6-tetramethylpiperidin-4-yl-methyl)-benzene, 1,4-bis-(1-benzyl-2,2,6,6-tetramethylpiperidin-4-yl-methyl)-benzene, 1,4-bis-(1-acetyl-2,2,6,6-tetramethylpiperidin-4-yl-methyl)-benzene, 1,4-bis-(1-ethylcarbamoyl-2,2,6,6-tetramethylpiperidin-4-yl-methyl)-benzene, 1,3-bis-(1-methyl-2,2,6,6-tetramethylpiperidin-4-yl-methyl)-benzene, 1,3-bis-(1-benzyl-2,2,6,6-tetramethylpiperidin-4-yl-methyl)-benzene, 1,3-bis-(2,3,6-trimethyl-2,6-diethylpiperidin-4-yl-methyl)-benzene, 4,4'-bis-(2,3,6-trimethyl-2,6-diethylpiperidin-4-yl-methyl)-diphenyl, 4,4'-bis-(1-allyl-2,2,6,6-tetramethylpiperidin-4-yl-methyl)-diphenyl, 4,4'-bis-(1-propargyl-2,2,6,6-tetramethylpiperidin-4-yl-methyl)-diphenyl, 4,4'-bis-(1-ethoxycarbonylmethyl-2,2,6,6-tetramethylpiperidin-4-yl-methyl)-diphenyl, 4,4'-bis-(1-tert.-butoxycarbonylmethyl-2,2,6,6-tetramethylpiperidin-4-yl-methyl)-diphenyl, 4,4'-bis-(1-benzyloxycarbonylmethyl-2,2,6,6-tetramethylpiperidin-4-yl-methyl)-diphenyl, 4,4'-bis-(1-oxyl-2,2,6,6-tetramethylpiperidin-4-yl-methyl)-diphenyl, 4,4'-bis-(2,2,6,6-tetramethylpiperidin-4-yl-methyl)-diphenylmethane, 4,4'-bis-(1-methyl-2,2,6,6-tetramethylpiperidin-4-yl-methyl)-diphenylmethane, 2,2-di-[p-(2,2,6,6-tetramethylpiperidin-4-yl-methyl)-phenyl]-propane and 4,4'-bis-(1-methyl-2,2,6,6-tetramethylpiperidin-4-yl-methyl)-diphenyl oxide.

The compounds of the formula I can be manufactured by catalytic hydrogenation of the corresponding piperidinylene compounds VI, which, in turn, can be manufactured by a Wittig-Horner reaction from the diphosphonates IV and the corresponding piperidones V. The diphosphonates IV are known compounds and can be obtained by a Michaelis-Arbusov reaction from the corresponding bis-(halogenomethyl) compounds III and trialkyl phosphites, as described, for example, in German Patent Specification No. 1,793,482.

The reaction (b) is carried out under the conditions generally known for Wittig-Horner reactions, such as are described, for example, in Houben-Weyl "Methoden der organischen Chemie" ("Methods of Organic Chemistry"), Volume V/1b, Stuttgart 1972, pages 395–401. Suitable solvents are, above all, polar anhydrous solvents, such as, for example, dimethylformamide, tetrahydrofurane, dioxane or dimethylsulphoxide. Suitable bases are anhydrous strong bases, for example NaOH, KOH or NaH, but above all alkali metal alkoxides, such as, for example, $CH_3ONa$, $CH_3OLi$, $C_2H_5ONa$ or $t-C_4H_9OK$. They are used in molar amounts. The reaction (b) is carried out at 20°–80° C. and preferably at 20°–50° C.

The compounds of the formula VI can also be manufactured by a classical Wittig reaction, in which a dihalide of the formula III is reacted with triphenylphosphine to give a phosphonium compound, which on treatment with 2 mols of an anhydrous base gives an ylide, which is then converted, by reaction with a piperidone V, into a compound of the formula VI.

The compounds of the formula VI are new compounds, which not only serve as intermediate products for the manufacture of the bis-piperidines of the formula I but also can themselves be used as light stabilisers for plastics.

The reaction (c) is carried out under the conditions customary for catalytic hydrogenations. Noble metal catalysts, such as Pt, Pd or Rh, above all those on a carrier, such as, for example, palladium-on-charcoal, are suitable as the catalyst.

The hydrogenation is preferably effected in solution since most compounds of the formula VI are solid. Suitable solvents are, for example, alcohols, such as methanol or ethanol, esters, such as ethyl acetate, or ethers, such as tetrahydrofurane or dioxane. The reaction is preferably carried out in lower alcohols.

In general, elevated temperatures and a high pressure are not required for the hydrogenation. It can be carried out under normal pressure or low pressure (up to 5 atmospheres gauge).

The hydrogenation products of the formula I are customarily isolated by separating off the catalyst and evaporating the solution. The compounds of the formula I are usually solid products and can be purified by recrystallisation.

The introduction of a substituent $R^2$, which is not hydrogen, can be effected either by using a correspondingly substituted piperidone V in the reaction (b) or by first manufacturing a compound of the formula I in which $R^2$ is hydrogen and converting this into a compound in which $R^2$ is not hydrogen. Suitable reactions for this purpose are the known reactions for introducing substituents into secondary amines, such as alkylation, (a) Michaelis-Arbusov reaction

III                  IV (R = lower alkyl, X = bromine or chlorine)

(b) Wittig-Horner reaction

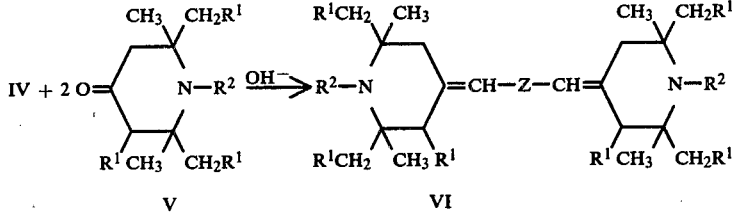

V             VI (c) Hydrogenation

alkenylation, alkinylation or aralkylation with the corresponding halogen compounds, acylation with carboxylic acid chlorides or carboxylic acid anhydrides and carbamoylation with isocyanates. Compounds in which $R^2$ is $-CH_2COOR^4$ or $-CH_2CONHR^5$ can be manufactured by reacting the NH-compounds with chloroacetic acid derivatives. Compounds in which $R^2$ is $-CH_2CH(R^6)OR^7$ can be manufactured by reacting the NH-compounds with ethylene oxide, propylene oxide or styrene oxide and optionally subsequently acylating. Compounds in which $R^2$ is an oxyl radical can be manufactured by oxidation of the NH-compounds with $H_2O_2$ or peroxycarboxylic acids. Those substituents $R^2$ which are hydrogenated under the conditions of the reaction (c), such as, for example, an oxyl radical or an alkenyl, alkinyl or alkenoyl radical, can be introduced only after the hydrogenation (c).

Further details of the manufacture of the compounds I can be taken from the examples which follow in the later part of the text.

The compounds of the formula I are outstanding light stabilisers for plastics and are distinguished by extreme stability to hydrolysis. It is indeed true that, when $R^2$ is an acyl group or contains an ester or amide radical, hydrolytic conversions of $R^2$ can arise, but the conversion products are also effective as light stabilisers and do not tend to migrate, since the bis-polyalkylpiperidine structure remains intact.

Examples of plastics which are damaged by the action of light and can be stabilised by the addition of the compounds of the formula I are the polymers listed on pages 12-14 of German Offenlegungsschrift No. 2,456,864.

The stabilisation of polyolefines and styrene polymers and of polyurethanes is of particular importance and the bispolyalkylpiperidines of the formula I are outstandingly suitable for this. Examples of such polymers are high density polyethylene and low density polyethylene, polypropylene, ethylene/propylene copolymers, polystyrene, styrene/butadiene/acrylonitrile copolymers, mixtures of polyolefines or of styrene polymers, and polyurethanes based on a polyether or polyester, in the form of lacquers, elastomers or foams.

The stabilisers are added to the plastics in a concentration of 0.01 to 5% by weight, calculated relative to the materials to be stabilised. Preferably, 0.03 to 1.5, and particularly preferentially 0.2 to 0.6, % by weight of the compounds, calculated relative to the material to be stabilised, are incorporated into the latter.

The incorporation can be effected after the polymerisation, for example by mixing the compounds, and optionally further additives, into the melt by the methods customary in industry, before or during shaping, or by applying the dissolved or dispersed compounds to the polymer, optionally with subsequent evaporation of the solvent.

The compounds can also be added to the plastics to be stabilised in the form of a master batch which contains these compounds, for example in a concentration of 2.5 to 25% by weight.

In the case of crosslinked polyethylene, the compounds are added prior to crosslinking.

In addition to the compounds of the formula I, yet further known stabilisers can also be added to the plastics. These can be, for example, antioxidants, light stabilisers or metal deactivators, or also co-stabilisers, such as, for example, those of the phosphorous acid ester type. Furthermore, other additives customary in plastics technology, such as, for example, flameproofing agents, antistatic agents, plasticisers, lubricants, blowing agents, pigments, reinforcing materials or fillers, can be added. Individual examples of such known and customary additives are listed in German Offenlegungsschrift No. 2,349,962, page 25-32.

The invention therefore also relates to the plastics which are stabilised by the addition of 0.01 to 5% by weight of a compound of the formula I and which optionally can also contain other known and customary additives. The plastics stabilised in this way can be used in very diverse forms, for example as films, fibres, tapes or profiles or as binders for lacquers, adhesives or putties.

The manufacture and use of the compounds according to the invention is described in more detail in the examples which follow. In these examples parts denote parts by weight and % denote percentages by weight. The temperatures are given in degrees centigrade.

EXAMPLES 1-5

Manufacture of bis-piperidinylidene compounds 5.7 g of sodium methoxide were introduced, in portions, into a solution, which had been warmed to 40° C., of 15.6 g of 2,2,6,6-tetramethyl-piperid-4-one and 20 g of 4,4'-bis-(dimethoxyphosphonomethyl)-diphenyl in 150 ml of dimethylformamide, whilst stirring, the temperature being kept between 40° and 45° C. by slight external cooling. After adding the sodium methoxide, the reaction mixture was stirred for a further 14 hours at room temperature. 250 ml of water were then added slowly to the reaction mixture, whilst stirring, the mixture was cooled to 0° C. and after one hour the precipitate which had formed was filtered off and rinsed with 50 ml of dimethylformamide/water (1:1). After drying in vacuo at 60° C., the compound thus obtained was crystallised from hexane and pure 4,4'-bis-(2,2,6,6-tetramethylpiperidin-4-ylidenemethyl)-diphenyl (compound No. 1) with a melting point of 136°-138° was obtained.

The following bis-piperidinylidene compounds of the formula $$\begin{array}{c}CH_3\ CH_3 \\ R^2-N \end{array}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!=CH-Z-CH=\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\begin{array}{c}CH_3\ CH_3 \\ N-R^2 \\ CH_3\ CH_3\end{array}$$

were manufactured in an analogous manner.

| Compound No. | Z | $R^2$ | Melting point |
|---|---|---|---|
| 2 | 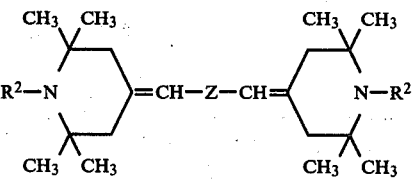 | $CH_3$ | 130°-131° |
| 3 |  | H | 90°-92° |

-continued

| Compound No. | Z | R² | Melting point |
|---|---|---|---|
| 4 | –⟨benzene⟩– | H | 119°–120° |
| 5 | –⟨benzene⟩– | CH₃ | 118°–119° |

EXAMPLE 6

4,4'-Bis-(2,2,6,6-tetramethylpiperidin-4-yl-methyl)-diphenyl 28.2 g of 4,4'-bis-(2,2,6,6-tetramethylpiperidin-4-ylidene-methyl)-diphenyl (compound No. 1) were dissolved in 280 ml of pure methanol and, after adding 2.5 g of palladium-on-charcoal (5% of Pd), catalytically hydrogenated at room temperature and under a hydrogen excess pressure of about 0.1 bar, the hydrogenation ceasing after about 1 hour when 99% of the theoretical amount of hydrogen had been taken up. For working up, the hydrogenation catalyst was filtered off, the methanol was distilled off in vacuo and the crystalline residue was recrystallised from hexane, pure 4,4'-bis-(2,2,6,6-tetramethylpiperidin-4-yl-methyl)-diphenyl (compound No. 6) with a melting point of 128°–129° being obtained.

EXAMPLES 7–11

Manufacture of bis-piperidines

The bis-piperidines which follow were manufactured under the process conditions of Example 6 by catalytic hydrogenation of the corresponding bis-piperidinylidene compounds.

$$R^2-N\diagdown\text{piperidine}\diagdown-CH_2-Z-CH_2-\diagdown\text{piperidine}\diagdown N-R^2$$

| Compound No. | Z | R² | Melting Point |
|---|---|---|---|
| 7 | –⟨biphenyl⟩– | CH₃ | 148°–149° |
| 8 | –⟨phenyl⟩– | H | 58°–60° |
| 9 | –⟨phenyl⟩– | H | 126°–127° |
| 10 | –⟨phenyl⟩– | CH₃ | 136°–137° |
| 11 | –⟨phenyl⟩–CH₂–⟨phenyl⟩– | CH₃ | 128°–130° |

EXAMPLES 12–14

N-Acylation of bis-piperidines 9.2 g of 4,4'-bis-(2,2,6,6-tetramethylpiperidin-4-yl-methyl)diphenyl (compound No. 6) in 80 ml of acetic anhydride and 2 drops of pyridine were heated at 70°–75° C. for 26 hours with stirring. For processing, the reaction mixture was filtered; the filtrate was freed in vacuo as completely as possible from acetic anhydride; the residue was dissolved in dichloromethane, and the solution was washed repeatedly with water, with 10% sodium bicarbonate solution and again with water. After drying of the dichloromethane solution over sodium sulphate, the solvent was distilled off, and the residue was recrystallised from acetonitrile to yield 4,4'-bis-(1-acetyl-2,2,6,6-tetramethylpiperidin-4-yl-methyl)-diphenyl, m.p. 174°–176° C. (compound No. 12).

The following were obtained analogously:
1,4-bis-(1-propionyl-2,2,6,6-tetramethylpiperidin-4-yl-methyl)benzene, m.p. 144°–146° C. from compound 9 and propionic acid anhydride (compound 13) and
1,4-bis-(1-acetyl-2,2,6,6-tetramethylpiperidin-4-yl-methyl)benzene, m.p. 126°–127° C. from compound No. 9 and acetic anhydride (compound No. 14).

EXAMPLE 15–22

N-Alkylation of bis-piperidines 8.72 g of benzyl bromide were added dropwise in the course of one hour to a mixture of 9.6 g of 1,4-bis-(2,2,6,6-tetramethylpiperidin-4-yl-methyl)-benzene (compound No. 9) 7.6 g of finely powdered potassium carbonate and 0.5 g of potassium iodide in 50 ml of ethyl methyl ketone, at the boil (bath temperature about 100° C.), whilst stirring, and the reaction mixture was stirred at this temperature for a total of 96 hours. For working up, the reaction mixture was filtered at the boiling point to remove the sediment (potassium bromide and a little potassium carbonate) and the filter residue was repeatedly rinsed with dichloromethane. The combined filtrates were freed from the solvent in vacuo, and the crystalline residue was recrystallised from ethyl methyl ketone to yield 1,4-bis(1-benzyl-2,2,6,6-tetramethylpiperidin-4-yl-methyl)-benzene, m.p. 207°–208° C. (compound No. 15).

The following N-substituted compounds were obtained analogously by reaction of the bis-piperidine 2, 6 or 9 with the corresponding halogen compounds:

4,4′-bis-(1-allyl-2,2,6,6-tetramethyl-piperidin-4-ylidenemethyl)-diphenyl, m.p. 186°–187° (compound No. 16), 4,4′-bis-(1-allyl-2,2,6,6-tetramethyl-piperidin-4-yl-methyl)diphenyl, m.p. 184°–186° (compound No. 17), 4,4′-bis-(1-propargyl-2,2,6,6-tetramethyl-piperidin-4-yl-methyl)diphenyl, m.p. 175°–177° (compound No. 18), 4,4′-bis-(1-hexyl-2,2,6,6-tetramethyl-piperidin-4-yl-methyl)diphenyl, m.p. 119°–120° C. (compound No. 19), 1,4-bis-[1-(2-methyl-but-2-enyl)-2,2,6,6-tetramethyl-piperidin-4-yl-methyl)]-benzene, m.p. 210°–212° (compound No. 20), 4,4′-bis-(1-ethoxycarbonylmethyl-2,2,6,6-tetramethyl-piperidin-4-yl-methyl)-diphenyl, m.p. 123°–124° (compound No. 21) and 1,4-bis-(1-octyl-2,2,6,6-tetramethyl-piperidin-4-yl-methyl)benzene, m.p. 78°–79° (compound No. 22).

EXAMPLE 23

100 parts of polypropylene powder (Moplen, fibre grade, from the firm Montedison) are homogenised for 10 minutes at 200° C., in a Brabender plastograph, with 0.2 part of octadecyl β-(3,5-di-tert.-butyl-4-hydroxy-phenyl)-propionate and 0.25 part of one of the stabilisers shown in the following Table 1. The composition thus obtained is removed from the kneader as quickly as possible and is pressed in a toggle press to give 2–3 mm thick sheet. A portion of the resulting pressed blank is cut out and pressed between two high-gloss aluminium sheets, using a manual hydraulic laboratory press, for 6 minutes at 260° under a pressure of 12 tons to give a 0.5 mm thick sheet, which is immediately quenched in cold water. The 0.1 mm thick test sheet is produced from this 0.5 mm sheet under precisely the same conditions. Specimens 60×44 mm in size are now punched from this test sheet and exposed in the Xenotest 150. These specimens are taken from the exposure apparatus at regular intervals and their carbonyl content is tested in an IR spectrophotometer. The increase in the carbonyl extinction at 5.85μ during exposure is a measure of the photooxidative degradation of the polymer (see L. Balaban et al., J. Polymer Sci., Part C, 22, 1059–1071 (1969)) and from experience is associated with a deterioration of the mechanical properties of the polymer. The time taken to reach a carbonyl extinction of about 0.3, at which point the comparison sheet is brittle, is taken as a measure of the protective action.

The protective action of the stabilisers according to the invention can be seen from the following Table 1:

Table 1

| Compound No. | Exposure time in hours until the carbonyl extinction is 0.30 |
| --- | --- |
| without light stabiliser | 1200 |
| 6 | 5100 |
| 7 | 5200 |
| 8 | >4500 |
| 9 | >7700 |
| 10 | >7700 |
| 12 | >3600 |
| 13 | >4500 |

What is claimed is:

1. A compound of the formula I

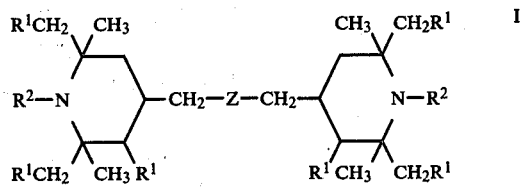

in which $R^1$ denotes hydrogen or alkyl with 1–4 C atoms, $R^2$ denotes hydrogen, an oxyl radical, alkyl with 1–12 C atoms, alkenyl with 3–6 C atoms, alkynyl with 3–6 C atoms, 2,3-epoxypropyl, aralkyl or alkaralkyl with 7–11 C atoms or one of the groups —CO—$R^3$, —CH$_2$COOR$^4$, —COOR$^4$, —CONHR$^5$, —CH$_2$CONHR$^5$ or —CH$_2$CH(R$^6$)OR$^7$, $R^3$ denotes hydrogen, alkyl with 1–6 C atoms, alkenyl with 2–4 C atoms, alkynyl with 2–4 C atoms or aralkyl or alkaralkyl with 7–15 C atoms, $R^4$ denotes alkyl with 1–12 C atoms, alkenyl with 3–6 C atoms, aralkyl with 7–8 C atoms or cyclohexyl, $R^5$ denotes alkyl with 1–18 C atoms, aralkyl or alkaralkyl with 7–15 C atoms, phenyl or alkylphenyl with 6–8 C atoms or cyclohexyl, $R^6$ denotes hydrogen, methyl or phenyl, $R^7$ denotes hydrogen or an alkanoyl, alkenoyl, aroyl or alkaroyl group with up to 18 C atoms and Z denotes a phenylene group or a group of the formula II

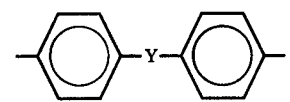

in which Y represents a direct bond or one of the groups —CH$_2$—, —C(CH$_3$)$_2$— or —O—, and the salts of such a compound of the formula I with inorganic or organic acids and complexes of a compound of the formula I with nickel compounds.

2. A compound according to claim 1, of the formula I, in which $R^1$ is hydrogen.

3. A compound according to claim 1, of the formula I, in which $R^2$ denotes hydrogen, alkyl with 1–6 C atoms, alkenyl with 3–5 C atoms, propargyl, benzyl, acetyl, propionyl, butyroyl, acryloyl, methacryloyl or crotonyl.

4. A compound according to claim 3, of the formula I, in which $R^2$ denotes hydrogen, methyl, allyl or benzyl.

5. A compound according to claim 1, of the formula I, in which Z denotes phenylene or para-diphenylene.

6. The compound according to claim 1, which is 1,4-Bis-(2,2,6,6-tetramethyl-piperidin-4-yl-methyl)-benzene.

7. The compound according to claim 1, which is 1,4-Bis-(1-methyl-2,2,6,6-tetramethyl-piperidin-4-yl-methyl)-benzene.

8. The compound according to claim 1, which is 1,4-Bis-(1-benzyl-2,2,6,6-tetramethyl-piperidin-4-yl-methyl)-benzene.

9. The compound according to claim 1, 1,4-Bis-(1-acetyl-2,2,6,6-tetramethyl-piperidin-4-yl-methyl)-benzene.

10. A compound of the formula VI

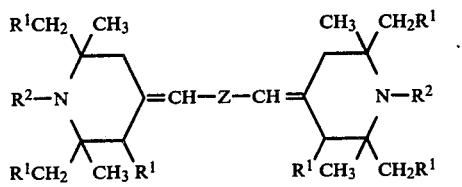

wherein $R_1$ denotes hydrogen or alkyl with 1–4 C atoms, $R_2$ denotes hydrogen, an oxyl radical, alkyl with 1–12 C atoms, alkenyl with 3–6 C atoms, alkynyl with 3–6 C atoms, 2,3-epoxypropyl, aralkyl or alkaralkyl with 7–11 C atoms or one of the groups —CO—$R^3$, —CH$_2$COOR$^4$, —COOR$^4$, —CONHR$^5$, —CH$_2$CONHR$^5$ or —CH$_2$CH($R^6$)OR$^7$, $R^3$ denotes hydrogen, alkyl with 1–6 C atoms, alkenyl with 2–4 C atoms, alkynyl with 2–4 C atoms of aralkyl or alkaralkyl with 7–15 C atoms, $R^4$ denotes alkyl with 1–12 C atoms, alkenyl with 3–6 C atoms, aralkyl with 7–8 C atoms or cyclohexyl, $R^5$ denotes alkyl with 1–18 C atoms, aralkyl or alkaralkyl with 7–15 C atoms, phenyl or alkylphenyl with 6–8 C atoms of cyclohexyl, $R^6$ denotes hydrogen, methyl or phenyl, $R^7$ denotes hydrogen or an alkanoyl, aroyl or alkaroyl group with up to 18 C atoms and Z denotes a phenylene group or a group of the formula II

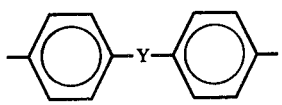

in which Y represents a direct bond or one of the groups —CH$_2$—, —C(CH$_3$)$_2$— or —O—, and the salts of such a compound of the formula I with inorganic or organic acids and complexes of a compound of the formula I with nickel compounds.

11. A compound according to claim 10, of the formula VI, in which $R^1$ denotes hydrogen, $R^2$ denotes hydrogen or methyl, Z denotes phenylene or a group of the formula II and Y denotes —CH$_2$—, C(CH$_3$)$_2$— or —O—.

12. A plastic stabilised against degradation by light, which contains 0.01 to 5% by weight of a compound of the formula I

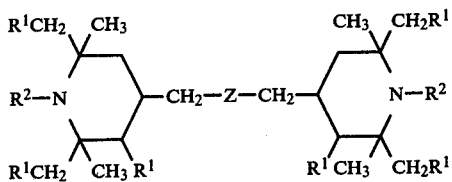

wherein $R_1$ denotes hydrogen or alkyl with 1–4 C atoms, $R_2$ denotes hydrogen, an oxyl radical, alkyl with 1–12 C atoms, alkenyl with 3–5 C atoms, alkynyl with 3–5 C atoms, 2,3-epoxypropyl, aralkyl or alkaralkyl with 7–11 C atoms or one of the groups —CO—$R^3$, —CH$_2$COOR$^4$, —COOR$^4$, —CONHR$^5$, —CH$_2$CONHR$^5$ or —CH$_2$CH($R^5$)OR$^7$, $R^3$ denotes hydrogen, alkyl with 1–6 C atoms, alkenyl with 2–4 C atoms, alkynyl with 2–4 C atoms or aralkyl or alkaralkyl with 7–15 C atoms, $R^4$ denotes alkyl with 1–12 C atoms, alkenyl with 3–8 C atoms, aralkyl with 7–8 C atoms or cyclohexyl, $R^5$ denotes alkyl with 1–18 C atoms, aralkyl or alkaralkyl with 7–15 C atoms, phenyl or alkylphenyl with 6–8 C atoms or cyclohexyl, $R^6$ denotes hydrogen, methyl or phenyl, $R^7$ denotes hydrogen or an alkanoyl, aroyl or alkaroyl group with up to 18 C atoms and Z denotes a phenylene group or a group of the formula II

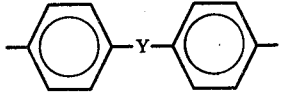

in which Y represents a direct bond or one of the groups —CH$_2$—, —C(CH$_3$)$_2$— or —O—, and the salts of such a compound of the formula I with inorganic or organic acids and complexes of a compound of the formula I with nickel compounds.

13. Stabilised plastic according to claim 12 wherein the plastic is a polyolefin, styrene polymer or polyurethane.

14. A plastic stabilised against degradation by light, which contains 0.01 to 5% by weight of a compound of the formula VI

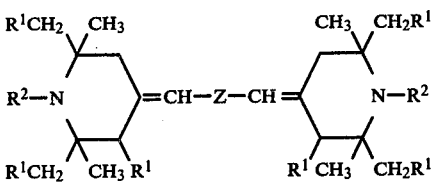

wherein $R_1$ denotes hydrogen or alkyl with 1–4 C atoms, $R_2$ denotes hydrogen, an oxyl radical, alkyl with 1–12 C atoms, alkenyl with 3–6 C atoms, alkynyl with 3–6 C atoms, 2,3-epoxypropyl, aralkyl or alkaralkyl with 7–11 C atoms or one of the groups —CO—$R^3$, —CH$_2$COOR$^4$, —COOR$^4$, —CONHR$^5$, —CH$_2$CONHR$^5$ or —CH$_2$CH($R^6$)OR$^7$, $R^3$ denotes hydrogen, alkyl with 1–6 C atoms, alkenyl with 2–4 C atoms, alkynyl with 2–4 C atoms or aralkyl or alkaralkyl with 7–15 C atoms, $R^4$ denotes alkyl with 1–12 C atoms, alkenyl with 3–5 C atoms, aralkyl with 7–8 C atoms or cyclohexyl, $R^5$ denotes alkyl with 1–18 C atoms, aralkyl or alkaralkyl with 7–15 C atoms, phenyl or alkylphenyl with 6–8 C atoms or cyclohexyl, $R^6$ denotes hydrogen, methyl or phenyl, $R^7$ denotes hydrogen or an alkanoyl, aroyl or alkaroyl group with up to 18 C atoms and 2 denotes a phenylene group or a group of the formula II

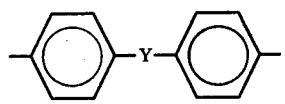

in which Y represents a direct bond or one of the groups —CH$_2$—, — C(CH$_3$)$_2$— or —O—, and the salts of such a compound of the formula I with inorganic or organic acids and complexes of a compound of the formula I with nickel compounds.

15. The stabilized plastic according to claim 14 wherein the plastic is a polyolefin, styrene polymer or polyurethane.

* * * * *